United States Patent [19]

Debrie

[11] Patent Number: 5,389,618

[45] Date of Patent: Feb. 14, 1995

[54] MIXTURES OF PARTICULAR LMW HEPARINIC POLYSACCHARIDES FOR THE PROPHYLAXIS/TREATMENT OF ACUTE THROMBOTIC EVENTS

[75] Inventor: Roger Debrie, Rieux, France

[73] Assignee: Rhone-Poulenc Rorer S.A., Antony, France

[21] Appl. No.: 92,577

[22] Filed: Jul. 16, 1993

Related U.S. Application Data

[63] Continuation of Ser. No. 721,315, Jun. 26, 1991, abandoned.

[30] Foreign Application Priority Data

Jun. 26, 1990 [FR] France .................. 90 08013

[51] Int. Cl.⁶ .................. A61K 31/725; C08B 37/10
[52] U.S. Cl. .......................... 514/56; 514/54; 536/21; 536/55.3
[58] Field of Search .............. 514/54, 56; 536/21, 536/55.3

[56] References Cited

U.S. PATENT DOCUMENTS

| | | | |
|---|---|---|---|
| 4,981,955 | 1/1991 | Lopez | 536/55.3 |
| 4,987,222 | 1/1991 | DeAmbrosi et al. | 536/55.3 |
| 4,990,502 | 2/1991 | Lormeau et al. | 536/55.3 |
| 5,019,649 | 5/1991 | Lormeau et al. | 536/21 |

FOREIGN PATENT DOCUMENTS 0040144 11/1981 European Pat. Off. .
0380719 8/1990 European Pat. Off. .

OTHER PUBLICATIONS

Oestergaard et al; Chemical Abstracts 107:541e (1987).
Fareed et al; Chemical Abstracts 109:31559n (1988).
Bender et al; Chemical Abstracts 109:31802m (1988).
Tew et al; Chemical Abstracts 110:50607p (1989).
Fareed et al; Haemostasis 18 (suppl. 3):3–15 (1988).
Barrowcliffe et al; ACTA Chir. Scand. Suppl. 543:57–64 (1988).
Ofosu; Haemostasis 20 (suppl. 1):180–192 (1990).
Hirsh; Adv. Appl. Biotechnol. Ser. 11 (Protein C Relat. Anticoagulants 67–82 (1990).

*Primary Examiner*—John W. Rollins
*Assistant Examiner*—Kathleen Kahler Fonda
*Attorney, Agent, or Firm*—Burns, Doane, Swecker & Mathis

[57] ABSTRACT

Heterogeneous intimate admixtures of sulfated heparinic polysaccharides, well suited for the prophylaxis/treatment of acute thrombotic episodes in a human patient, comprise immixture of sulfated polysaccharides having a weight average molecular weight less than that of heparin and which include from 9% to 20% of polysaccharide chains having a molecular weight less than 2,000 daltons and from 5% to 20% of polysaccharide chains having a molecular weight greater than 8,000 daltons, the ratio between the weight average molecular weight and the number average molecular weight thereof ranging from 1.3 to 1.6.

32 Claims, No Drawings

MIXTURES OF PARTICULAR LMW HEPARINIC POLYSACCHARIDES FOR THE PROPHYLAXIS/TREATMENT OF ACUTE THROMBOTIC EVENTS

This application is a continuation, of application Ser. No. 07/721,315, filed Jun. 26, 1991, now abandoned.

BACKGROUND Of THE INVENTION

1. Field of the Invention

The present invention relates to novel mixtures of low molecular weight (LMW) polysaccharides and, more especially, to novel mixtures of LMW heparinic polysaccharides well adopted for the prevention of venous thromboses.

2. Description of the Prior Art

The heparins are biologically active agents of the glycosaminoglycan family, extracted from natural sources, and have valuable anticoagulant and anti-thrombotic properties. In particular, they are useful in the treatment of postoperative venous thromboses. However, in their native state, the heparins present a number of disadvantages which limit the extent of their effective use. Indeed, the marked anticoagulant activity of the heparins can cause hemorrhaging, and their sensitivity to certain serum factors such as pf4 mandates the administration of relatively large doses thereof. Hence, it is necessary to favor the antithrombotic activity, attributed, notably, to the antiprothrombinase activity, at the expense of the anticoagulant activity, attributed to the antithrombin effect.

Thus, it is known to this art to fragment the heparins into molecules of lower average molecular weights. For example, European Patent EP 40,144 describes the preparation of mixtures of sulfated polysaccharides of which heparin is comprised, including an ethylenic double bond at one end of their polymer chains and having a weight average molecular weight ranging from 2,000 to 10,000 daltons. These mixtures are produced by depolymerization and saponification of a heparin ester. They are said to have high antithrombotic activity and an overall anticoagulant activity lower than that of heparin.

However, one of the principal difficulties associated with the heparins is that they are very heterogeneous products. Therefore, it is difficult to assess the contribution of each of the species to the activity of heparin, to determine the behavior of these species during depolymerization and, finally, to control the structure of such species and their respective proportions in the final products. For these reasons, it has not to date been possible to resolve completely satisfactorily the difficulties indicated above. In particular, the processes described in the prior art, and especially in EP 40,144, do not permit the production of mixtures possessing the requisite pharmacological properties for improved therapeutic applications, namely, a sufficiently long plasma half-life, a fairly high absorption rate, a high bioavailability or, alternatively, a low clearance.

Other processes are also known to this art for the fragmentation of heparin with a view towards diminishing the adverse effects thereof (compare Johnson et al, *Thrombos.Haemostas.Stuttg.*, 35, 586 (1976); Lane et al, *Thrombosis Research*, 16, 651; Lasker et al, U.S. Pat. No. 3,766,167)). Each appears to indicate that the desired activity is favored when the degree of fragmentation of heparin increases (see also published European Patent Application EP 301,618 relating to pentasaccharides possessing antithrombotic activity).

Likewise, recent studies on the mechanism of action of the heparins in thrombin formation have demonstrated an influence of the average molecular weight of the heparins on their activity in vitro (Béguin et al, *Thromb. Haemost.*, 61, 30 (1989)). It is reported that low molecular weight heparins tend to possess an antiprothrombinase activity, and heparins of higher molecular weight an antithrombin activity.

It too has been proposed to this art to fractionate the heparins in order to extract mixtures of more homogeneous average molecular weight therefrom. European Patent Application EP 337,327 thus describes a process for preparing oligosaccharide fragments derived from heparin, permitting mixtures having a reduced molecular weight dispersion to be obtained. According to this process, the fractions having a molecular weight below 3,000 daltons are first removed, whereby the final product is devoid of fragments containing less than 10 to 16 saccharides, and then the species having a molecular weight above 7,000 daltons. This treatment is said to provide a more homogeneous final mixture having decreased anticoagulant activity while at the same time preserving the desired antithrombotic activity.

Nonetheless, these final mixtures continue to elicit a residual hemorrhagic effect, or too low an antithrombotic response. In addition, the prior art is essentially silent in respect of which particular properties have to be combined to provide optimum biological activity. This is reflected in the above publication, where the authors conclude, "We do not know what combination of the properties of heparin is optimal. The precise characterization of different preparations and the correlation of these properties with clinical observations might possibly provide an answer."

SUMMARY OF THE INVENTION

Accordingly, a major object of the present invention is the provision of novel combinatory immixtures of particular heparinic polysaccharide fractions, such novel immixtures being especially useful for the prophylaxis and treatment of acute thrombotic events/episodes.

Indeed, it has now surprisingly and unexpectedly been found that mixtures of both high and low molecular weight heparinic polysaccharides, nonetheless having an average molecular weight less than that of heparin, exhibit desirable balance of antithrombotic/anticoagulant activity. Contrary to the direction of the prior art, a certain fraction of relatively high molecular weight heparinic polysaccharides and a certain degree of heterogeneity are required to provide such balance of biological activity.

A pharmacokinetic study of the mixtures of the invention evidences that they combine a plurality of essentially advantageous properties.

For example, the mixtures of the invention exhibit a half-life longer than other known preparations, and also longer than mature heparin. Moreover, in relation to the latter, it will be appreciated that the half-life of the mixtures of the invention is independent of the dose injected. This is desirable in that the effect elicited is much more predictable than in the case of heparin.

In addition, in humans, the mixtures of the invention display excellent bioavailability, as measured by the anti-Xa activity. Thus, this value is approximately 30 IU for heparin, but is approximately 90 IU for the mixtures of the invention. This too is desirable in that it permits the doses administered to be reduced and the therapeutic potential to be improved.

Moreover, another desirable property of the mixtures of the invention is their high rate of absorption. This permits virtually instantaneous biological activity to be attained, and hence affords greater safety in treatment by providing for more rapid patient protection.

Another characteristic of the mixtures according to the invention is their low clearance compared with other products and with mature heparin. As a result of their chemical structure, their molecular weight or their sulfate content, these mixtures effectively display a particular pronounced resistance to degradation (desulfation, hydrolysis) and to elimination, which further enhances their therapeutic availability.

The preparations of the invention additionally exhibit an increased residence time compared with the heparin starting material. This property is reflected by a prolongation of the time during which the product remains active in vivo, and hence in a better therapeutic efficacy.

Too, these preparations also exhibit a reduced sensitivity to serum factors, which enhances their duration of action in vivo and permits them to be used in low doses.

These especially desirable properties are provided by controlling, during the preparation of the mixtures according to the invention, certain structural aspects of the heparinic species present therein, as well as their molecular weight distribution. The mixtures thereby obtained have a favorable ratio of the fractions of high to those of low molecular weights, which endows them with the requisite antithrombotic properties with but slight risk of hemorrhagic effect.

This characteristic of the invention is expressed both by the percentage of high molecular weight chains and of low molecular weight chains and by the ratio of the weight average molecular weight of the mixtures to their number average molecular weight, which reflects the molecular dispersion.

Briefly, the present invention features combinatory immixtures of sulfated polysaccharides having the general structure of the polysaccharides of which heparin is composed, such polysaccharides having a weight average molecular weight less than that of heparin and comprising from 9% to 20% of polymer chains of molecular weight less than 2,000 daltons and from 5% to 20% of polymer chains of molecular weight greater than 8,000 daltons, and in which the ratio weight average molecular weight/number average molecular weight ranges from 1.3 to 1.6.

DETAILED DESCRIPTION OF THE PREFERRED EMBODIMENTS OF THE INVENTION

More particularly according to the present invention, it has now also been found that it is possible to improve the properties of the mixtures further by decreasing their content of impurities. As is known to this art, the majority of the heparins contain contaminants such as nucleic acids, polypeptides or various polysaccharides. Among the latter, chondroitin sulfates and heparan or dermatan sulfate are especially representative. Each of these contaminants, as a result of its very high molecular weight and as a result of the substituents which it bears or its degree of sulfation, is capable of interfering during the preparation of the product (e.g., in the depolymerization sequence) and adversely affecting the final molecular weight distribution, or directly the activity, by modifying the respective proportions of the active polymer chains.

The present invention, by means of particular pretreatment, not only provides for the removal of such impurities, but also enhances the desirable properties of the mixtures thus pretreated. The effect of this pretreatment may be measured using dermatan sulfate as a control impurity.

In a preferred embodiment of the present invention, the subject mixtures of sulfated heparinic polysaccharides have the desirable properties indicated above and contain less than 2% of dermatan sulfate.

In another preferred embodiment of the invention, the mixtures of sulfated polysaccharides have a weight average molecular weight ranging from approximately 3,500 daltons to approximately 5,500 daltons.

Also preferably, the backbones of the sulfated polysaccharides comprising the mixtures according to the invention have a 2-O-sulfo-4-enopyranosuronic acid at one of their chain ends.

This invention also features a process for preparing mixtures of sulfated polysaccharides having a weight average molecular weight less than that of heparin, comprising from 9% to 20% of polymer chains having a molecular weight less than 2,000 daltons and from 5% to 20% of polymer chains having a molecular weight greater than 8,000 daltons, and in which the ratio weight average molecular weight/number average molecular weight ranges from 1.3 to 1.6.

This process comprises (a) first salifying a starting material heparin in an aqueous medium by means of a long-chain quaternary ammonium salt, (b) next esterifying the salt thus produced to form an ester having a degree of esterification ranging from 9.5% to 14%, and (c) then depolymerizing such ester having a degree of esterification ranging from 9.5% to 14%.

Thus, it has now been determined that the level of depolymerization, and hence the molecular characteristics of the final product, may be controlled by varying the degree of esterification of the heparin salt starting material.

According to the invention, it is thus possible to directly and reproducibly produce mixtures of sulfated polysaccharides having the characteristics indicated above.

The heparin starting material employed in the process of the invention is preferably a porcine heparin, and, in particular, a porcine mucosal heparin. It has also been determined that the activity of the final mixtures could vary substantially in consequence of the origin of the heparin starting material. In particular, when the heparin starting material is of bovine origin, mixtures are produced having an anticoagulant activity greater than that of mixtures produced from porcine intestinal mucosal heparin.

Furthermore, in an especially advantageous embodiment of the invention, the heparin starting material is preliminarily precipitated by means of an alcohol upstream of the salification thereof. This pretreatment enables the content of impurities of the chondroitin sulfate or heparan sulfate type to be decreased.

A representative alcohol providing good results is, e.g., methanol.

The degree of purity of the heparin sodium may then be determined by steric exclusion liquid chromatography.

This preliminary step permits, in particular, the preparation of a heparin having a dermatan sulfate content of less than 2%.

More particularly, the salification of the starting heparin is carried out in the following manner.

The heparin salt may be prepared by the interaction of a stoichiometric excess of the corresponding salt with a heparin sodium, in an aqueous medium, at a temperature in the region of 20° C. Advantageously, the quaternary ammonium salt used is preferably a benzethonium salt such as, in particular, benzethonium chloride, which facilely reacts with the heparin sodium.

In the second step (b) of the subject process, the esterification is preferably carried out under the following conditions.

The partial ester of heparin in salt form, the degree of esterification of which ranges from 9.5% to 14%, may be prepared by esterification of the long-chain quaternary ammonium salt of heparin in a chlorinated organic solvent, in the presence of a chlorine derivative. In addition, the efficiency of the reaction is increased by controlling the proportions of the various reactants and the reaction temperature and time.

Advantageously, the partial ester of heparin is an aromatic ester.

Also preferably, the chlorine derivative is benzyl chloride and the chlorinated solvent is either chloroform or methylene chloride.

To attain a degree of esterification ranging from 9.5% to 14%, it can be especially advantageous to use approximately 1 part by volume of chlorine derivative per 1 part by weight of the heparin salt in 3 to 5 parts by volume of chlorinated organic solvent, and to carry out the reaction for a period of time ranging from 15 to 48 hours at a temperature of from 25° to 45° C., and preferably from 30° to 40° C.

In another preferred embodiment of the invention, the partial ester of heparin is in the form of a sodium salt.

The esters thereby formed may be recovered by precipitation by means of an alcohol such as, in particular, methanol, in the presence of sodium acetate. Preferably, from 1 to 1.2 volumes of alcohol are used per volume of reaction medium. The degree of esterification of the ester may then be determined by high performance liquid chromatography. In particular, in the case of the benzyl ester, the amount of benzyl alcohol produced by saponification of the ester at 0° C. may be measured.

The final step (c) of the process of the invention is advantageously carried out in the following manner.

Preferably, the depolymerization is carried out by treating the ester with a strong base in aqueous solution. More preferably, sodium hydroxide is used therefor.

Advantageously, the weight ratio base/ester ranges from 0.05 to 0.2, and preferably from 0.08 to 0.15.

The temperature of the reaction medium is adjusted to a value ranging from 50° to 70° C., and preferably from 55° to 65° C., and the reaction is carried out for a period of time ranging from 30 minutes to 3 hours, and preferably from 1 to 2 hours.

It is also preferable to carry out the reaction in a medium in which the weight ratio water/ester ranges from 15 to 30.

In an especially preferred embodiment of the depolymerization of the invention, one part by weight of an aromatic ester of heparin as prepared in step (b), in salt form, the degree of esterification of which ranges from 9.5% to 14%, is admixed with from 0.08 to 0.15 part by weight of sodium hydroxide, as well as with from 20 to 30 parts by weight of water, and the resulting admixture is then maintained at a temperature of from 55° to 65° C. for from 1 to 2 hours.

The product may then be recovered by neutralization of the reaction medium with a dilute inorganic acid, and preferably hydrochloric acid, and precipitation in the presence of an alcohol such as methanol.

In this manner, an immixture of sulfated heparinic polysaccharides is directly and reproducibly prepared, containing:

(1) from 9% to 20% of polymer chains having a molecular weight less than 2,000 daltons, and
(2) from 5% to 20% of polymer chains having a molecular weight greater than 8,000 daltons, and having an average molecular weight ranging from 3,500 to 5,500 daltons and a ratio weight average molecular weight/number average molecular weight ranging from 1.3 to 1.6.

The mixtures of the present invention are advantageously used as antithrombotic agents, typically when formulated with a pharmaceutically acceptable carrier or diluent therefor.

In particular, they are useful therapeutic compositions for the prevention of venous thromboses in patient risk situations. This is also valid for prolonged-risk situations. More especially, administration of these mixtures provides, for the first time, at fixed doses, a decrease in the risks of acute thrombotic events attendant orthopedic surgery. This risk, which is 70% in the absence of any treatment and approximately 25% on administration of heparin, is only about 10% on administration of the mixtures of the invention, or even less.

Similarly, when injected into the tubing of an artificial kidney, the subject mixtures can reduce the likelihood of any thromboses developing therein. This latter application may be extended to the prevention of thromboses in surgical equipment.

Another advantageous therapeutic use of the mixtures of the invention is in the prevention of acute arterial thrombotic events, particularly myocardial infarction.

Moreover, an especially advantageous application of the mixtures according to the present invention is in their use in a postoperative regimen for the prevention of venous thromboses in surgical patients. This application is particularly desirable, since it permits avoiding the risks of hemorrhage during an operation, and the problems of type and dose of anesthetic, which characterize a preoperative regimen of prevention.

These collective properties demonstrate the therapeutic potential of the immixtures of the invention.

In order to further illustrate the present invention and the advantages thereof, the following specific examples are given, it being understood that same are intended only as illustrative and in nowise limitative.

In said examples to follow, the analytical procedures included:

ASSAY TECHNIQUES:

The molecular weights and molecular weight distributions of the products were determined by high pressure liquid chromatography using two columns in series, i.e., those marketed under the trademarks TSK G 3000SW (30×0.75 cm) and Lichrosorb 100 Diol 10u (25×0.75 cm), or TSK G 2000SW, coupled to a refractometer detector. The solvent used was a 0.3M phosphate buffer pH 7, and the flow rate was 0.7 ml/min. The system was calibrated with standards prepared by fractionation of enoxaparin (PHARMUKA) by exclusion chromatography on agarose-polyacrylamide (IBF) according to the technique described by Barrowcliffe et al, *Thromb. Res.*, 12, 27–36 (1977–78) or D.A. Lane et al, *Thromb. Res.*, 12, 257–271 (1977–78). The results were calculated using GPC6 software (Perkin Elmer).

The overall anticoagulant activity of the mixtures was measured by turbidimetry using the Primary International Standard of low molecular weight heparin. The anti-factor Xa (antithrombotic) activity was measured by the amidolytic method on a chromogenic substrate, described by Teien et al, *Thromb. Res.*, 10, 399–410 (1977), using the Primary International Standard of low molecular weight heparin.

EXAMPLE 1

This example illustrates the preliminary step of treatment of heparin sodium, enabling the content of impurities of the chondroitin sulfate and heparan sulfate type to be reduced.

Methanol (80 ml) was added to commercial heparin (sodium salt) (10 g) dissolved in water (100 ml) containing sodium chloride (3 g). After precipitation, the product obtained was filtered off, rinsed and then dried. The degree of purity of the heparin sodium thereby obtained was measured by steric exclusion liquid chromatography, using two columns in series, marketed under the trademarks TSK 2000SW (60×0.75 cm) and TSK 3000 SW (60×0.75 cm), coupled to a UV detector adjusted to 206 nm. The mobile phase employed was 0.5M aqueous sodium sulfate solution flowing at a rate of 1 ml.min$^{-1}$. The test sample was compared with a control heparin containing dermatan sulfate (2%).

Under the conditions described above, the heparin obtained contained less than 2% of dermatan sulfate.

EXAMPLE 2

This example illustrates the preparation of the quaternary ammonium salt of heparin.

A solution of benzethonium chloride (25 g) in water (125 ml) was added to a solution of heparin sodium (10 g) prepared as in Example 1, containing less than 2% of dermatan sulfate, in water (100 ml). The product obtained at room temperature was then filtered off, washed with water and thereafter dried.

In identical manner, the benzethonium salt of a heparin which had not been subjected to the treatment of Example 1 was prepared.

EXAMPLE 3

This example illustrates the preparation and properties of the mixtures according to the invention.

1. Esterification:

Benzyl chloride (15 ml) was added to a solution of benzethonium heparinate (15 g), preliminarily treated according to the procedure of Example 1, in methylene chloride (75 ml). The solution was heated to a temperature of 35° C., which was maintained for 25 hours. A 10% solution (90 ml) of sodium acetate in methanol was then added, the mixture was filtered and the product was washed in methanol and dried. Heparin benzyl ester (6.5 g) was thereby obtained in the form of a sodium salt, the degree of esterification of which, determined as described above, was 13.3%.

2. Depolymerization:

The heparin benzyl ester (10 g) obtained above in the form of a sodium salt was dissolved in water (250 ml). To this solution, heated to 62° C., sodium hydroxide (0.9 g) was added. The temperature was maintained for 1 hour, 30 minutes, at 62° C. The reaction mixture was then cooled to about 20° C. and neutralized by adding dilute hydrochloric acid. The concentration of the reaction medium was then adjusted to 10% with respect to sodium chloride. The product was finally precipitated in methanol (750 ml), filtered off and dried. A heparin possessing the following structural characteristics was thereby obtained:

(a) Weight average molecular weight: 3,900 daltons,
(b) Molecular weight distribution: (i) 20% of polymer chains of molecular weight less than 2,000 daltons,
   (ii) 5.5% of polymer chains of molecular weight greater than 8,000 daltons,
(c) Dispersion: d=1.39,
(d) Anti-Xa activity: 106 IU,
(e) Anticoagulant activity: 22.6 IU.

EXAMPLE 4

Following the procedure of Example 3, beginning with esters having a degree of esterification ranging from 9.5 to 14%, solutions of depolymerized heparin having the following structural characteristics were prepared:

Solution A:
(a) Weight average molecular weight: 4,425 daltons,
(b) Molecular weight distribution:
   (i) 12.4% of polymer chains of molecular weight less than 2,000 daltons,
   (ii) 9.3% of polymer chains of molecular weight greater than 8,000 daltons,
(c) Dispersion: d=1.37,
(d) Anti-Xa activity: 102 IU,
(e) Anticoagulant activity: 33 IU.

Solution B:
(a) Weight average molecular weight: 4,579 daltons,
(b) Molecular weight distribution:
   (i) 11.2% of polymer chains of molecular weight less than 2,000 daltons,
   (ii) 10.4% of polymer chains of molecular weight greater than 8,000 daltons,
(c) Dispersion: d=1.37,
(d) Anti-Xa activity: 104 IU,
(e) Anticoagulant activity: 37 IU.

Solution C:
(a) Weight average molecular weight: 4,446 daltons,
(b) Molecular weight distribution:
   (i) 12.6% of polymer chains of molecular weight less than 2,000 daltons,
   (ii) 9.5% of polymer chains of molecular weight greater than 8,000 daltons,
(c) Dispersion: d=1.38,
(d) Anti-Xa activity: 100 IU,
(e) Anticoagulant activity: 32 IU.

EXAMPLE 5

This example illustrates the preparation of a mixture not in accordance with the invention.

1. Esterification:

Benzyl chloride (12 ml) was added to a solution of benzethonium heparinate (15 g), treated preliminarily according to the procedure of Example 1, in methylene chloride (60 ml). The solution was heated to a temperature of 28° C., which was maintained for 30 hours. A 10% solution (90 ml) of sodium acetate in methanol was then added, the mixture was filtered and the product was washed with methanol and dried. Heparin benzyl ester (6.3 g) was thereby obtained in the form of a sodium salt. The degree of esterification of this product, determined by measurement, in high performance liquid chromatography, of the quantity of benzyl alcohol liberated on saponification of the ester at 0° C., was 9.2%.

2. Depolymerization:

The heparin benzyl ester (10 g) obtained above in the form of a sodium salt was dissolved in water (200 ml). To this solution, heated to 58° C., sodium hydroxide (1.1 g) was added. The temperature was maintained for 1 hours at 58° C. The reaction mixture was then cooled to about 20° C. and neutralized by adding dilute hydrochloric acid. The concentration of the reaction medium was then adjusted to 10% with respect to sodium chloride. The product was finally precipitated in methanol (600 ml), filtered off and dried. A heparin possessing the following structural characteristics was thereby obtained:

(a) Weight average molecular weight: 5,425 daltons,
(b) Molecular weight distribution:
  (i) 9.6% of polymer chains of molecular weight less than 2,000 daltons,
  (ii) 19.5% of polymer chains of molecular weight greater than 8,000 daltons,
(c) Dispersion: d=1.44,
(d) Anti-Xa activity: 122 IU,
(e) Anticoagulant activity: 68.6 IU.

These results, which evidenced a high anticoagulant activity, demonstrated the superiority of the mixtures prepared according to the invention and possessed the noted characteristics.

EXAMPLE 6

This example illustrates the increase in stability, in vivo, of the mixtures of the invention, expressed by their plasma half-life.

A first pharmacokinetic study was carried out on volunteers between 21 and 30 years of age. Subcutaneous injections of doses ranging from 20 to 80 mg/ml were performed. At intervals of time, samples were drawn (4.5 ml) and stored at approximately 4° C. The samples were then centrifuged for 15 minutes at 2,300 g and the platelet-poor plasma was separated and frozen prior to analysis. The half-life of the mixtures was then determined by measuring the anti-Xa activity. The results obtained were as follows:

(1) From the mixtures produced in Examples 3 and 4:
   40 mg dose: in 75% of the cases, the half-life was longer than 4 hours, and was even longer than 4½ hours in approximately 45% of the cases;
   60 mg dose: in 75% of the cases, the half-life was longer than 3.7 hours.
(2) Under identical dosage conditions, intact heparin injected intravenously possessed a half-life of approximately 0.6 hours.
(3) When the product was prepared according to the process described in European Patent EP 40,144, the half-life was longer than 4½ hours in 17% of the cases.
(4) A second study carried out under similar conditions on 20 patients provided the following results for the mixtures according to the present invention:
   40 mg dose: in 80% of cases, the half-life was longer than 4 hours, and it was longer than 4½ hours in approximately 40% of the cases;
   20 mg dose: in 60% of the cases, the half-life was longer than 3.9 hours.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A heterogeneous intimate admixture of sulfated heparinic polysaccharides, such sulfated polysaccharides having a weight average molecular weight less than that of heparin and said admixture consisting essentially of from 9% to 20% of polysaccharide chains having a molecular weight less than 2,000 daltons
from 5% to 20% of polysaccharide chains having a molecular weight greater than 8,000 daltons, and
from 60–86% of polysaccharide chains having a molecular weight of between 2,000 and 8,000 daltons,
the ratio between the weight average molecular weight and the number average molecular weight thereof ranging from 1.3 to 1.6
said admixture (i) exhibiting a bioavailability and antithrombotic activity greater than heparin and (ii) having an average molecular weight of between approximately 3,500 and 5,500 daltons.

2. The heterogeneous polysaccharide admixture as defined by claim 1, comprising less than 2% of dermatan sulfate.

3. The heterogeneous polysaccharide admixture as defined by claim 1, such sulfated polysaccharides comprising a 2-O-sulfo-4-enopyranosuronic endgroup.

4. The heterogeneous polysaccharide admixture as defined by claim 1, exhibiting an anti-Xa activity of about 90 IU.

5. The heterogeneous polysaccharide admixture as defined by claim 1, comprising sulfated polysaccharides of porcine heparin origin.

6. The heterogeneous polysaccharide admixture as defined by claim 1, comprising polysaccharides of bovine heparin origin.

7. A process for the preparation of the heterogeneous polysaccharide admixture as defined by claim 1, comprising (a) salifying a heparin with a long-chain quaternary ammonium salt in an aqueous medium, (b) esterifying the salt thus produced to a degree of esterification ranging from 9.5% to 14%, and then (c) depolymerizing such ester having a degree of esterification ranging from 9.5% to 14%.

8. The process as defined by claim 7, comprising (b) esterifying said salt in a chlorinated organic solvent, in the presence of a chlorine compound.

9. The process as defined by claim 8, said chlorinated organic solvent comprising chloroform or methylene chloride and said chlorine compound comprising benzyl chloride.

10. The process as defined by claim 8, said esterification step (b) comprising mixing 1 part by weight of said heparin salt with about 1 part by volume of said chlorine compound in from 3 to 5 parts by volume of said chlorinated organic solvent at a temperature ranging from 25° C. to 45° C.

11. The process as defined by claim 10, said temperature ranging from 30° to 40° C.

12. The process as defined by claim 7, said depolymerization step (c) comprising treating said ester with a strong base in aqueous solution.

13. The process as defined by claim 12, wherein said strong base and said ester are present in a weight ratio which ranges from 0.05 to 0.2.

14. The process as defined by claim 13, said ratio ranging from 0.08 to 0.15.

15. The process as defined by claim 12, wherein water in said aqueous solution and said ester are present in a weight ratio which ranges from 15 to 30.

16. The process as defined by claim 12, wherein said depolymerization is carried out at a temperature adjusted to a value ranging from 50° to 70° C. and said depolymerization is carded out therein for from 30 minutes to 3 hours.

17. The process as defined by claim 16, said temperature being adjusted to a value ranging from 55° to 65° C. and said depolymerization being carried out for from 1 to 2 hours.

18. The process as defined by claim 7, comprising (a) salifying the heparin with a benzethonium salt.

19. The process as defined by claim 18, said benzethonium salt comprising benzethonium chloride.

20. The process as defined by claim 7, the partial ester prepared in step (b) comprising an aromatic ester.

21. The process as defined by claim 7, the partial ester prepared in step (b) comprising a sodium salt thereof.

22. The process as defined by claim 7, said starting material heparin having been precipitated from an alcohol.

23. The heterogeneous intimate admixture of sulfated heparinic polysaccharides produced by the process as defined by claim 7.

24. A method for the prevention of thrombotic episodes in a human patient, comprising administering to a human in need of such prevention, a therapeutically effective amount of the heterogeneous polysaccharide admixture as defined by claim 1.

25. A method for the prevention of venous thromboses in a postoperative human patient, comprising administering to such patient a therapeutically effective amount of the heterogeneous polysaccharide admixture as defined by claim 1.

26. The method as defined by claim 24, such human suffering risk of myocardial infarction.

27. A therapeutic composition of matter useful for the prevention of thrombotic episodes in a human, comprising the heterogeneous polysaccharide admixture as defined by claim 1 and a therapeutically acceptable carrier or diluent therefor.

28. The heterogeneous polysaccharide admixture as defined by claim 1, exhibiting an anti-Xa activity of about 100 IU.

29. A method for the treatment of thrombotic episodes in a human, comprising administering to a human in need of such treatment, a therapeutically effective amount of the heterogeneous polysaccharide admixture as defined by claim 1.

30. A therapeutic composition of matter useful for the treatment of thrombotic episodes in a human, comprising the heterogeneous polysaccharide admixture as defined by claim 1 and a therapeutically acceptable carrier or diluent therefor.

31. A heterogenous intimate admixture of sulfated heparinic polysaccharides, such sulfated polysaccharides having a weight average molecular weight less than that of heparin and said admixture comprising:

from 9% to 20% of polysaccharide chains having a molecular weight less than 2,000 daltons, from 5% to 20% of polysaccharide chains having a molecular weight greater than 8,000 daltons, and from 60% to 86% of polysaccharide chains having a molecular weight of between 2,000 and 8,000 daltons, the ratio between the weight average molecular weight and the number average molecular weight thereof ranging from 1.3 to 1.6, said admixture (i) exhibiting a bioavailability and antithrombotic activity greater than heparin, (ii) having an average molecular weight of between approximately 3,500 and 5,500 daltons, and (iii) including less than 2% of dermatan sulfate.

32. A heterogeneous intimate admixture of sulfated heparinic polysaccharides, such sulfated polysaccharides having a weight average molecular weight less than that of heparin and said admixture consisting essentially of:

from 9% to 20% of polysaccharide chains having a molecular weight less than 2,000 daltons, from 5% to 20% of polysaccharide chains having a molecular weight greater than 8,000 daltons, and from 60% to 86% of polysaccharide chains having a molecular weight of between 2,000 and 8,000 daltons, the ratio between the weight average molecular weight and the number average molecular weight thereof ranging from 1.3 to 1.6, said admixture (i) exhibiting a bioavailability and antithrombotic activity greater than heparin and (ii) having an average molecular weight of between approximately 3,500 and 5,500 daltons, said admixture being prepared by a process comprising the steps of:

(a) salifying a heparin with a long-chain quaternary ammonium salt in an aqueous medium, (b) esterifying the salt thus produced to a degree of esterification ranging from 9.5% to 14%, and (c) depolymerizing such ester having a degree of esterification ranging from 9.5% to 14%.

* * * * *